(12) United States Patent
Golz-Berner et al.

(10) Patent No.: US 8,252,297 B2
(45) Date of Patent: Aug. 28, 2012

(54) COSMETIC AND DERMATOLOGIC OXYGEN CARRIER SYSTEM

(75) Inventors: Karin Golz-Berner, Monaco (MC); Leonhard Zastrow, Monaco (MC); Roselyne Moyon, Le Cannet (FR)

(73) Assignee: Coty B.V., Haarlem (NL)

( * ) Notice: Subject to any disclaimer, the term of this patent is extended or adjusted under 35 U.S.C. 154(b) by 923 days.

(21) Appl. No.: 10/596,237

(22) PCT Filed: Dec. 1, 2004

(86) PCT No.: PCT/EP2004/013856
§ 371 (c)(1),
(2), (4) Date: Jun. 5, 2006

(87) PCT Pub. No.: WO2005/053636
PCT Pub. Date: Jun. 16, 2005

(65) Prior Publication Data
US 2007/0189988 A1 Aug. 16, 2007

(30) Foreign Application Priority Data

Dec. 8, 2003 (DE) .................................. 103 58 306

(51) Int. Cl.
*A61K 8/02* (2006.01)
(52) U.S. Cl. ......................................................... 424/401
(58) Field of Classification Search .................... 424/401
See application file for complete search history.

(56) References Cited

U.S. PATENT DOCUMENTS

| | | | |
|---|---|---|---|
| 4,569,784 A | 2/1986 | Moore | |
| 5,219,844 A | 6/1993 | Peyman et al. | |
| 5,637,318 A * | 6/1997 | Gross et al. | 424/450 |
| 5,643,601 A * | 7/1997 | Gross et al. | 424/450 |
| 5,736,505 A * | 4/1998 | Manzo et al. | 512/2 |
| 5,811,083 A * | 9/1998 | Pelle et al. | 424/59 |
| 5,874,093 A | 2/1999 | Eliaz et al. | |
| 5,885,564 A | 3/1999 | Zastrow et al. | |
| 5,961,988 A * | 10/1999 | Zastrow et al. | 424/400 |
| 6,403,109 B1 * | 6/2002 | Stora | 424/401 |
| 6,419,909 B1 | 7/2002 | Lorant et al. | |
| 6,500,439 B1 | 12/2002 | Morita et al. | |
| 6,576,623 B1 * | 6/2003 | Nakanishi et al. | 514/63 |
| 2003/0103922 A1 | 6/2003 | Garrison et al. | |
| 2003/0235548 A1 * | 12/2003 | Lu | 424/70.12 |

FOREIGN PATENT DOCUMENTS

| | | |
|---|---|---|
| DE | 4333561 A1 | 4/1995 |
| DE | 199 07 305 A1 * | 8/2000 |
| DE | 19907305 A1 | 8/2000 |
| EP | 0670159 A1 | 9/1995 |
| JP | 48096782 A | 12/1973 |
| JP | 58034033 A | 2/1983 |
| JP | 4224506 A | 8/1992 |
| JP | 5124951 A | 5/1993 |
| JP | 9503802 T | 4/1997 |
| JP | 2001192319 A | 7/2001 |
| JP | 2006500424 T | 1/2006 |
| WO | 93/01798 A1 | 2/1993 |
| WO | 94/00098 A1 | 1/1994 |
| WO | 9400098 | 1/1994 |
| WO | 9413783 | 6/1994 |
| WO | 9417588 | 8/1994 |
| WO | 9712852 A1 | 4/1997 |
| WO | 03/043598 A1 | 5/2003 |

OTHER PUBLICATIONS

Critical Care Medicine Tutorials, http://www.ccmtutorials.com/rs/oxygen/page02.htm, published 2002, accessed online Nov. 9, 2009.*
CRC Handbook of Chemistry and Physics, 87th edition, 1998. p. 1-40.*

* cited by examiner

*Primary Examiner* — Richard Schnizer
*Assistant Examiner* — Audrea Buckley
(74) *Attorney, Agent, or Firm* — Norris McLaughlin & Marcus PA

(57) ABSTRACT

The invention relates to an oxygen carrier system which is suitable for applying gaseous oxygen to the skin in cosmetic and dermatological forms of application. Said system comprises 0.1 to 10 percent by weight of a liquid perfluorinated or partially fluorinated hydrocarbon or hydrocarbon mixture, 10 to 85 percent by weight of a liquid silicone polymer or silicone polymer mixture, and 5 to 25 percent by weight of an oil base or water base, all percentages being in relation to the total weight of the carrier system. Major moieties of the inventive system can be introduced without stability problems especially into silicone oil-containing formulations.

10 Claims, No Drawings

COSMETIC AND DERMATOLOGIC OXYGEN CARRIER SYSTEM

The invention relates to an oxygen carrier system suitable to apply gaseous oxygen in cosmetic and dermatologic forms of application onto the skin.

It is known to use perfluorocarbon compounds as oxygen carriers in cosmetic forms of application. WO 94/0098 describes asymmetric lamellar aggregates consisting of perfluorocarbons and phospholipids with a phosphatidylcholin content of at least 30 percent in weight. In modern cosmetic formulations, silicone oils are increasingly being used in order to accomplish certain advantageous properties, such as light weight, no stickiness, richness. Such formulations can, however, incorporate only small concentrations of the known oxygen carrier systems which do not exceed 5 percent in weight because a higher percentage will then lead to stability problems in the formulations. Lower concentrations of such known oxygen carrier systems require correspondingly lower oxygen content in the formulation and correspondingly in respect of the effectiveness for the skin.

Another disadvantage of the known systems is the fact that relatively high concentrations of the carrier system of 10 to 40 percent in weight are required in silicone oil-free formulations in order to ensure oxygen release quantities over longer periods of time of 8 to 40 weeks.

An object of the invention is the provision of a new oxygen carrier system that can be used at will in silicone oil-containing cosmetic or dermatologic formulations without stability problems for the formulation and where its effectiveness is markedly increased as far as oxygen release is concerned.

In accordance with the invention, the cosmetic and dermatologic oxygen carrier system is characterised in that it consists of a liquid perfluorinated or partially fluorinated hydrocarbon or hydrocarbon mixture with a moiety of 0.1-10 percent in weight, a liquid silicon polymer or silicone polymer mixture with a moiety of 10-85 percent in weight and an oil or water base with a moiety of 5-25 percent in weight, with all weight percentages being related to the total weight of the carrier system.

In an advantageous embodiment, the oxygen carrier system is loaded with an initial oxygen content of 150-950 mbar $O_2$ Preferably, the initial oxygen content is 250 to 400 mbar $O_2$ already in the presence of moieties of 2-5 percent in weight of perfluorinated hydrocarbon.

In another advantageous embodiment, the oxygen carrier system is loaded four weeks after the loading with an oxygen content of 5-40 percent by volume of the initial oxygen content, preferably 15-25 percent by volume.

The oxygen loading of a system according to the invention is in general done as follows: after the preparation of the carrier system, oxygen gas with a partial pressure of 180 to 600 mbar is bubbled through the entire composition while stirring with 200-400 r.p.m. and at ambient temperature (18-25° C.) over a period of 15 to 100 minutes, preferably 20 to 40 minutes followed by its incorporation into the respective cosmetic or dermatologic formulation.

While with the known oxygen carrier systems with phospholipids or with sphingomyelines (Cerasomes) which belong to the phospholipids, after an initial drop of the $O_2$ concentration after 24 h by about 30-50%, in the weeks thereafter a continuous drop of the concentration down to an equilibrium with the oxygen of the air occurs after 26 weeks, the carrier systems according to the invention maintain, after the 24 h drop by 30 to 50%, the $O_2$ concentration in the weeks thereafter over an essentially longer period of time and with higher moieties of 25 to 40%. After 8 weeks, measurements resulted in $O_2$ concentrations of 5 to 15% for the carrier system of the invention when compared to the initial content which then continue to remain approximately constant.

This means that an increased oxygen offer with a comparable concentration of the perfluorocarbons is available for a longer period of time and can thus be supplied to the skin cells. It is known that it is specifically the surface area of the skin up to a depth of 0.4 mm where most of the oxygen is absorbed not via the blood but via the oxygen of the air.

Advantageously, the oxygen carrier system of the invention can in addition contain tocopherol or a tocopherol derivative with a moiety of 0.01-1.5 percent by weight, related to the overall weight of the carrier system. Thus, a further improvement of the effectiveness in respect of the stability of the system in silicone oil-containing cosmetic formulations is accomplished. Suitable tocopherol derivatives are for instance tocopheryl acetate, tocopheryl palmitate, tocopheryl succinate, tocopheryl propionate, tocopheryl oleate, tocopheryl linolate or tocopheryl sorbate which may also be used as a mixture of the same or with tocopherol.

The oxygen carrier system according to the invention may surprisingly be incorporated in cosmetic or dermatologic formulations, in particular in those with silicone oils or silicone polymers, in concentration of up to 40 percent in weight without impairing the stability of the cosmetic or dermatologic formulation.

The liquid silicone polymer in the carrier system according to the invention on an oil base is advantageously a cyclic silicone oil or a mixture of cyclic silicone oils with other silicone oils.

The liquid silicone polymer in a carrier system on a water base is advantageously an aqueous suspension of silicone elastomers in combination with a methylpolysiloxane.

Particularly preferred are organosiliconeoxide polymers, such as methylpolysiloxanes as, for instance, BAR-SIL® 2001 (from Barnet, Englewood Cliffs, USA) or fluorosilicones which contain at least one trifluoroalkyl group in monomers, such as Gransil®, e.g. Gransil® FLD-55 (from Grant Ind., Inc., Elmwood Park, USA). The preferred silicone elastomer emulsion is the dimethicone/vinyldimethicone cross polymer (and) C12-12 Pareth-12 with a viscosity of about 5,000 mPa·s.

Other suitable silicone polymers are polydimethylcyclosiloxanes (e.g. cyclopentasiloxanes), mixtures of cyclopentasiloxanes with cyclohexasiloxanes (e.g. DC® 345), mixtures of cyclopentasiloxanes with high viscous Dimethiconol (e.g. DC® 1501), mixtures of polydimethylsiloxanes with viscosities ranging from 0,65-60,000 $mm^2s$ (e.g. DC® 200 Fluids).

The oil base of the carrier system is advantageously a vegetable oil, an ester, such as dicaprylyl carbonate (Cetiol CC), isodecyl neopentanoate (e.g. DUV VCI 10), neopentyl glycol diheptanoate (e.g. Lexfeel® 7), trimethylolpropane tricapry-late/tricaprate (e.g. Lexfeel®21) or a mixture thereof. Synthetic oils are particularly preferred.

The oxygen carrier is preferably a perfluorinated hydrocarbon, in particular perfluodecalin, F-butyltetrahydro-furane, perfluorotributylamine, perfluoromethyl-cyclopentane, perfluoro-1,3-dimethylcyclohexane, perfluoroperhydro-benzyldecaline, perfluoroperhydrophenanthrene, perfluorooctylbromide, Bis-fluoro-(butyl)ethene or $C_6$-$C_9$-perfluoroalkanes.

The moiety of the perfluorinated hydrocarbon or hydrocarbon mixture is preferably in the range of 1.5 to 6 percent by weight, related to the overall weight of the carrier system.

The moiety of the silicone polymer in the carrier system is advantageously 15 to 35 percent by weight.

Moreover, the carrier system contains advantageously at least one gelling agent with a viscosity in the range of 120,000 Pa·s to 300,000 Pa·s, in particular in a carrier system on an oil base.

Particularly preferred are gels, such as mineral oil-free gels with hydrogenated polyisobuten as base, for instance Versagel® (from Penreco, Dickinson, USA) or organic, modified montmorillonites, such as bentone gel.

The use of thickening agents in the carrier system is also preferred.

The following are preferably used as water thickening agents: xanthan gum, ammonium acryloyldimethyl laurate/VP copolymer, ammonium acryloyldimethyl laurate/Beheneth-25, methylacrylate copolymer (e.g. Aristoflex® AVC or HMB), homo- and copolymers of acrylic acid and polyalkenylpolyethers (e.g. Carbopol®-thickening agent) with a high molecular weight.

Different benton gels are suited as oil thickening agents, for instance C12-15 Alkyl Benzoate(and)Stearalkonium Hectorite (and)Propylene Carbonate, Isodecane(and) Disteardimonium Hectorite(and)Propylene Carbonate, Cyclopenta-siloxane(and)Disteardimonium Hectorite(and)SD Alcohol which can also be used in mixtures.

Thickening agents, such as hydrogenated polyisobuten (e.g. Versagel® ME 1600) with a viscosity of about 143,000 mPa·s (Brookfiled Viscosimeter, 25° C., Spindle T-C, 5 r.p.m.) can also be used.

The oxygen carrier system according to the invention can be incorporated into any cosmetic or dermatologic formulation, for instance such a topical formulation can have the form of a cream, a lotion, a self-tanning agent, a sun protection formulation for use before, during and after exposure to sun, of a mask, a gel, a spray.

In a cosmetic formulation, the moiety of the oxygen carrier system may amount to 1 to 25 percent by weight in relation to the overall weight of the formulation, preferably to 6 to 10%.

In a dermatologic formulation, the moiety of the oxygen carrier system may amount to 3 to 40 percent by weight, preferably to 6 to 35% in relation to the overall weight of the formulation.

The cosmetic or dermatologic formulations into which the oxygen carrier system of the invention can be incorporated may contain common inactive ingredients, carriers and active ingredients, e.g. inactive ingredients and carriers, such as water, preservatives, colorants, pigments with a colouring effect, thickening agents, fragrants, monovalent and polyvalent alcohols, esters, electrolytes, gelling agents, polar and non-polar oils, polymers, copolymers, emulsifiers, waxes, stabilisers.

Particularly suited are formulations which contain moieties of silicone oils >5%, preferably 6-70%, in particular 6-35%. The oxygen carrier system of the invention can be incorporated into such formulations without the risk of an instability of the formulation. All common silicone oils qualify as silicone oils in the formulation.

Cosmetic active ingredients include, inter alia, inorganic and organic sunscreen agents, free radical scavengers, moisturisers, vitamins, enzymes, active ingredients from plants, antioxidants, antiphlogistic natural active ingredients, disintegration products from yeasts or plant substances, manufactured by means of an ultrasound disintegration method pursuant to WO 94/13783, kaolin as well as kaolin modified with $SiO_2$ pursuant to WO 94/17588 and dihydroxyacetone. Another active ingredient for such a formulation with the oxygen carrier system according to the invention is a special preparation with a high factor of protection against free radicals which contains a product produced from the bark of Quebracho blanco by extraction and subsequent enzymatic hydrolysis which contains at least 90 percent by weight of proanthocyanidine oligomers and not more than 10 percent by weight of gallic acid, in micro-capsules, and a silkworm extract produced by extraction which extract contains the peptide cecropine, amino acids and a vitamin mixture and a non-ionic, cationic or anionic hydrogel or mixture of hydrogels, and one or more phospholipids, and water. This special preparation can also contain superoxide dismutase and cyclodextrine.

Furthermore, the invention relates to a method for preparation of a cosmetic oxygen carrier system characterised in that at least one part of a liquid silicone polymer is incorporated while stirring at 20 to 100 r.p.m. into at least one part of the oil or water base at a temperature ranging from 18 to 26° C., adding in addition while stirring at 10 to 80 r.p.m. a liquid perfluorinated or partially perfluorinated hydrocarbon or a hydrocarbon mixture stirring it for 3 to 30 minutes, adding, if appropriate, further constituents or remaining moieties of the mentioned constituents while stirring at 40 to 150 r.p.m. and homogenising the mixture for 20 to 150 seconds at maximally 3,000 r.p.m.

Advantageously, the carrier system is loaded in the procedure with gaseous oxygen up to a partial pressure of 150 to 950 mbar $O_2$.

The invention relates moreover to the use of a cosmetic oxygen carrier system consisting of a liquid perfluorinated or partially fluorinated hydrocarbon or hydrocarbon mixture with a moiety of 0.1-10 percent in weight, a liquid silicon polymer with a moiety of 35-85 percent in weight, an oil or water base with a moiety of 5-25 percent in weight, and, if appropriate, a tocopherol or tocopherol derivative with a moiety of 0.01 to 1.5 percent by weight with all weight percentages being related to the total weight of the carrier system in topical formulations, in particular in those with silicone oil contents of 5 to 25 percent by weight, related to the overall weight of the topical formulation.

The topical formulation advantageously has the form of a cream, a lotion, a self-bronzing agent, a sun protection formulation for use before, during and after exposure to sun, of a mask, a gel, a spray.

The invention will be described below in greater details by way of examples. All data are in percent by weight unless stated otherwise.

EXAMPLE 1

Preparation of the Oxygen Carrier System (SiOx I) on an Aqueous Base

Composition in percent by weight:

| (A) | Dimethicone | 20 |
|---|---|---|
| (B) | Trifluoromethyl C1-4 Alkyl Dimethicone | 35 |
| (C) | Perfluordecalin | 5 |
| (D) | Tocopherol | 0.4 |
| (E) | Dimethicone/Vinyldimethicone Crosspolymer (and) Cl2-14 Pareth-12 | 25 |
| (F) | Water | 14.6 |

While stirring, the relevant amount of (B) is slowly added to (A) at ambient temperature, and stirring is continued for a few minutes. While stirring, (C) is added, and stirring is continued for about 20 to 30 minutes. Thereafter, (E) is successively added while also slowly stirring, then (D) and finally (F). The mixture is homogenised at about 2,500 r.p.m. for 50 seconds. All steps were carried out at about 21-25° C.

Thereafter, gaseous oxygen with 400 mbar is bubbled through the mixture for 30 minutes while stirring at 280 r.p.m.

The obtained oxygen contents are measured with an Oxi 3000 (WTW GmbH, Weilheim, Germany).

EXAMPLE 2

Preparation of the Oxygen Carrier System (SiOx II) on an Oil Base

Composition in percent by weight:

| (A) | Cyclopentasiloxane | 10 |
|---|---|---|
| (B) | Dicapryl Carbonate | 10 |
| (C) | Perfluordecalin | 2 |
| (D) | Tocopherol | 0.5 |
| (E) | Hydrogenated Polyisobutene (and) Ethylene/Propylene/Styrene Copolymer (and) Butylene/-Ethylene/-Styrene Copolymer (Versagel ® ME1600) | 40 |
| (F) | Bentone Gel | 37.5 |

While stirring at 400 to 500 r.p.m., the relevant amount of (B) is slowly added to (A), and stirring is continued for a few minutes. (C) is added at 900 to 1,000 r.p.m., and stirring is continued for about 20 to 30 minutes. Thereafter, (D) is added, then (E) and finally (F). The mixture is homogenised at about 2,700 to 2,800 r.p.m. for 40 seconds. All steps were carried out at about 20-24° C.

Thereafter, gaseous oxygen with 450 mbar is bubbled through the mixture for 35 minutes while stirring at 300 r.p.m.

EXAMPLE 3

Body Foam (Mousse) I

| Water | up to 100% |
|---|---|
| Squalane | 0.01 |
| Butylene Glycol | 2.0 |
| Glycerol | 2.0 |
| PPG-5 Ceteth-20 | 1.0 |
| Decyl Glucoside | 3.0 |
| SiOx I of Example 1; 160 mbar $O_2$ | 6.0 |

The constituents were mixed at ambient temperature in the order as stated above and then transferred into a pump bottle with a special pump for mousse.

EXAMPLE 4

Body Foam (Mousse) II

The same constituents as in Example 3 and in addition 6% of silicone oil were processed in the same way into a body foam.

EXAMPLE 5

Self-Tanning Agent I O/W

| Phase A | |
|---|---|
| Water | up to 100% |
| Dihydroxyacetone | 5.0 |
| Glycerol | 2.0 |
| Phase B | |
| Dimethicone | 6.0 |
| Dimethicone/Vinyldimethicone Crosspolymer (and) C12-14 Pareth-12 | 25 |
| Cyclopentasiloxane Dimethiconol | 2.0 |
| Octyldodecyl Stearoyl Stearate | 2.5 |
| Phase C | |
| Preservative | 0.5 |
| Fragrance | 0.5 |
| Phase D | |
| SiOx II of Example 2; 210 mbar $O_2$ | 10 |

EXAMPLE 6

Self-Tanning Agent II (Example for Comparison)

| Phase A | |
|---|---|
| Water | up to 100 |
| Dihydroxyacetone | 5.0 |
| Glycerol | 2.0 |
| Phase B | |
| Dimethicone | 6.0 |
| Dimethicone/Vinyldimethicone Crosspolymer (and) C12-14 Pareth-12 | 5 |
| Cetiole CC | 20 |
| Octyldodecyl Stearoyl Stearate | 2.5 |
| Phase C | |
| Preservative | 0.5 |
| Fragrance | 0.5 |
| Asymmetric lamellar aggregates pursuant to WO94/0098 | 5 |

When attempting to increase the content of the aggregates mentioned last as oxygen carriers (180 mbar $O_2$) to more than 5%, the formulation became unstable and a phase seperation occurred.

EXAMPLE 7

Body Gel

| Water | up to 100 |
|---|---|
| Glycerol | 5 |
| Dimethicone | 15 |
| Propylene Glycol | 10 |
| Carbomere | 2 |
| Triethanolamine | 2 |
| Preservative | 0.5 |
| Fragrance | 0.2 |
| SiOx I of example 1; 254 mbar $O_2$ | 20 |

The constituents were successively added to each other and homogeneously mixed by stirring.

EXAMPLE 8

Skin Fluid Serum

| | |
|---|---|
| Water | up to 100 |
| Glycerol | 3 |
| Propylene Glycol | 5 |
| Carbomere | 1 |
| Silicone | 10 |
| Triethanolamine | 1 |
| Preservative | 0.5 |
| Fragrance | 0.2 |
| SiOx I of example 2; 215 mbar $O_2$ | 15 |

The constituents were successively added to each other and homogeneously mixed by stirring.

The invention claimed is:

1. Cosmetic or dermatologic formulation, comprising an oxygen carrier system at 6-10% by weight of the formulation, wherein the carrier system comprises, as a percentage of the carrier system: a liquid perfluorinated or partially fluorinated hydrocarbon or hydrocarbon mixture with a moiety of 0.1-10% by weight, a liquid silicone polymer or silicone polymer mixture with a moiety of 10-85% by weight and a water base with a moiety of 5-25% by weight, and the carrier system being loaded with gaseous oxygen at a partial pressure of 250-400 mbar $O_2$.

2. Formulation according to claim 1, wherein the carrier system is loaded with an oxygen content of 25-40% by volume of the initial oxygen content, as measured at a time four weeks after an initial loading.

3. Formulation according to claim 1, wherein the carrier system contains tocopherol or a tocopherol derivative with a moiety of 0.01-1.5% by weight, wherein the tocopherol derivative is selected from the group consisting of tocopheryl acetate, tocopheryl succinate, tocopheryl propionate, tocopheryl oleate, tocopheryl linolate, tocopheryl, tocopheryl palmitate, tocopheryl sorbate mixtures thereof and mixtures thereof with tocopherol.

4. Formulation according to claim 1, wherein the moiety of the liquid silicone polymer ranges from 15-35% by weight.

5. Formulation according to claim 1, wherein the carrier system contains at least a gelling or thickening agent or a mixture thereof.

6. Formulation according to claim 1, wherein the oxygen carrier is perfluorodecaline.

7. Formulation according to claim 1, wherein the moiety of the perfluorinated hydrocarbon or hydrocarbon mixture ranges from 1.5-6% by weight.

8. Formulation according to claim 1, further comprising a silicone oil with a moiety of 6-35%.

9. Formulation according to claim 1, wherein the liquid silicone polymer has a moiety of 35-85% by weight.

10. The topical formulation according to claim 9 wherein the topical formulation has the form of a cream, a lotion, a self-tanning agent, a sun protection formulation for use before, during and after the exposure to sun, of a mask, a gel, a spray.

* * * * *